US008580925B2

(12) United States Patent
Kannagi et al.

(10) Patent No.: US 8,580,925 B2
(45) Date of Patent: Nov. 12, 2013

(54) METHOD FOR EXAMINING CARCINOMA AND ADENOMA

(75) Inventors: Reiji Kannagi, Nagoya (JP); Mineko Izawa, Seto (JP); Naoko Kimura, Nagoya (JP); Shunsuke Kurei, Nagano (JP); Kazue Watanabe, Nagano (JP)

(73) Assignees: Japan Science and Technology Agency, Saitama (JP); Local Government of Aichi Prefecture, Aichi (JP); Wako Pure Chemical Industries, Ltd., Osaka (JP)

( * ) Notice: Subject to any disclaimer, the term of this patent is extended or adjusted under 35 U.S.C. 154(b) by 3 days.

(21) Appl. No.: 11/795,328

(22) PCT Filed: Dec. 15, 2005

(86) PCT No.: PCT/JP2005/023015
§ 371 (c)(1),
(2), (4) Date: Jul. 16, 2007

(87) PCT Pub. No.: WO2006/077704
PCT Pub. Date: Jul. 27, 2006

(65) Prior Publication Data
US 2008/0096234 A1     Apr. 24, 2008

(30) Foreign Application Priority Data
Jan. 19, 2005    (JP) ................................. 2005-011151

(51) Int. Cl.
*C07K 16/00*       (2006.01)
(52) U.S. Cl.
USPC ..................................................... 530/387.1
(58) Field of Classification Search
None
See application file for complete search history.

(56) References Cited

U.S. PATENT DOCUMENTS

| 7,601,348 | B2 | 10/2009 | Kannagi et al. |
| 2002/0164748 | A1 | 11/2002 | Bistrup |
| 2007/0196874 | A1 | 8/2007 | Kannagi et al. |
| 2010/0015632 | A1 | 1/2010 | Kannagi et al. |

FOREIGN PATENT DOCUMENTS

| JP | 06-000093 | 1/1994 |
| JP | 06-046878 | 2/1994 |
| JP | 11-313684 | 11/1999 |
| WO | 2005/019827 | 3/2005 |
| WO | WO2005/019827 | 3/2005 |
| WO | WO2006/077704 | 7/2006 |

OTHER PUBLICATIONS

Hemmerich et al., Immunity vol. 15, p. 237-47, 2001.*
Seko et al. Glycobiology, vol. 12, p. 379-388, 2002.*
Kanoh et al. Glycocoj J. vol. 23, p. 453-460, 2006.*
Izawa et al. Cancer Research, vol. 60, p. 1410-1416, 2000.*
Lee et al. Glycobiology vol. 13, p. 245-254, 2002.*
Mitsuoka et al. J. Bio. Chem. vol. 273, p. 11225-11233, 1998.*
Search Report dated Feb. 14, 2006 for International Application No. PCT/JP2005/023015 filed Dec. 15, 2005.
Annette Bistrup et al., "Detection of a Sulfotransferase (HEC-GlcNAc6ST) in High Endothelial Venules of Lymph Nodes and in High Endothelial Venule Like Vessels within Ectopic Lymphoid Aggregates," American Journal of Pathology, May 2004, pp. 1635-1644, vol. 164, No. 5, American Society for Investigative Pathology, Bethesda, Maryland USA.
Mineko Izawa et al., "Expression of Sialyl 6-Sulfo Lewis X is Inversely Correlated with Conventional Sialyl Lewis X Expression in Human Colorectal Cancer,"Cancer Research, Mar. 1, 2000, pp. 1410-1416, vol. 60, American Associated for Cancer Research, Baltimore, Maryland USA.
Akira Seko at al., "Biochemical Differences Between Two Types of N-acetylglucosamine:→6sulfotransferases in Human Colonic Adenocarcinomas and the Adjacent Normal Mucosa: Specific Expression of a GlcNAc:→6sulfotransferase in Mucinous Adenocarcinoma," Glycobiology, 2000, pp. 919-929, vol. 10, No. 9.
Akira Seko at al., "Ectopic Expression of a GlcNAc 6-O-sulfotransferase, G1cNAc6ST-2, in Colonic Mucinous Adenocarcinoma," Glycobiology, 2002, pp. 379-388, vol. 12, No. 6.
Kenji Uchimura et al., "Specificities of N-Acetylglucosamine-6-O-sulfotransferases in Relation to L-selectin Ligand Synthesis and Tumor-associated Enzyme Expression," The Journal of Biological Chemistry, Feb. 8, 2002, pp. 3979-3984, vol. 277, No. 6, American Society for Biochemistry and Molecular Biology, Baltimore, Maryland.
Philip R. Streeter et al., "Immunohistologic and Functional Characterization of a Vascular Addressin Involved in Lymphocyte Homing into Peripheral Lymph Nodes" The Journal of Cell Biology, Nov. 1988, pp. 1853-1862, vol. 107, Rockfeller University Press, New York USA.
Richard E. Bruehl et al., "Minimal Sulfated Carbohydrates for Recognition by L-selectin and the MECA-79 Antibody," The Journal of Biological Chemistry, Oct. 20, 2000, pp. 32642-32648, vol. 275, No. 42, American Society for Microbiology, Washington DC, USA.
Jiunn-Chern Yeh et al., "Novel Sulfated Lymphocyte Homing Receptors and Their Controlby a Corel Extension β1,3-N-Acerylglucosaminyltransferase," Cell, Jun. 2001, pp. 957-969, vol. 105, Issue 7, Cell Press, Cambridge, Massachusetts, USA.

(Continued)

*Primary Examiner* — Sean Aeder
(74) *Attorney, Agent, or Firm* — Jenkins, Wilson, Taylor & Hunt, P.A.

(57) ABSTRACT

[PROBLEMS] To provide examination methods and reagents able to detect efficiently cancer patients and patients at high risk of cancer.
[MEANS FOR SOLVING PROBLEMS] Significant differences in the distribution of GlcNAc-6-sulfotransferase isozymes, sulfation enzymes of sugar residues, between non-carcinoma tissues and carcinoma tissues or adenoma tissues were discovered. The discovery is evidently applicable to detect carcinomas and adenomas (except colorectal carcinomas and colorectal adenomas) specifically by assaying a certain range of GlcNAc-6-sulfated sugar residue groups in tissues of patients and in fecal samples. Examination of carcinomas and adenomas is possible by the use of antibodies reacting specifically with GlcNAc-6-sulfated sugar residues specifically synthesized by enzymes present in carcinoma and adenoma tissues.

3 Claims, 5 Drawing Sheets

(56) References Cited

OTHER PUBLICATIONS

Reiji Kannagi at al., "Carbohydrate-Mediated Cell Adhesion in Cancer Metastasis and Angiogenesis," Cancer Sci, May 2004, pp. 377-384, vol. 95, No. 5.

Bistrup, A., et al., Detection of a Sulfotransferase (HEC-GlcNAc6ST) in High Endothelial Venules of Lymph Nodes and in High Endothelial Venule-Like Vessels within Ectopic Lymphold Aggregates: Relationship to the MECA-79 Epitope. *American Journal of Pathology*, Vo. 164, No. 5 pp. 1635-1644 (2004).

Bruehl, R. E., et al., Minimal Sulfated Carbohydrates for Recognition by L-selectin and the MECA-79 Antibody. *The Journal of Biological Chemistry*. vol. 275, No. 42 pp. 32642-32648 (2000).

Kimura, N., et al., Reconstitution of functional L-selectin ligands on a cultured human endothelial cell line by cotransfection of $\alpha 1 \rightarrow 3$ fucosyltransferase VII and newly cloned GlcNAcβ:6-sulfotransferase cDNA. *Proceedings of the National Academy of Sciences of USA*. vol. 96 pp. 4530-4535 (1999).

Seko, A., et al., Ectopic expression of a GlcNAc 6-0-sulfotransferase, GlcNAc6ST-2, in colonic mucinous adenocarcinoma. *Glycobiology*. vol. 12, No. 6 pp. 379-388 (2002).

Supplementary European Search Report corresponding to European Application No. 05816850.1-2404 dated Jan. 28, 2009.

Uchimura, K., et al., Specificities of N-Acetylglucosamine-6-O-sulfotransferases in Relation to L-selectin Ligand Synthesis and Tumor-associated Enzyme Expression. *The Journal of Biological Chemistry*. vol. 277, No. 6 pp. 3979-3984 (2002).

Lee et al., Cloning and characterization of a mammalian N-acetylglucosamine-6-sulfotransferase that is highly restricted to intestinal tissue. *Biochemical and Biophysical Research Communications*. vol. 2, No. 263 pp. 543-549 (1999).

Notice of Allowance corresponding to U.S. Appl. No. 10/568,544 dated May 29, 2009.

Official Action corresponding to U.S. Appl. No. 10/568,544 dated Nov. 13, 2007.

Official Action corresponding to U.S. Appl. No. 10/568,544 dated Jul. 22, 2008.

Official Action corresponding to U.S. Appl. No. 10/568,544 dated Dec. 31, 2008.

Seko et al., Biochemical differences between two types of N-acetylglucosamine:→6sulfotransferases in human colonic adenocarcinomas and the adjacent normal mucosa: specific expression of a G1cNAc:→6sulfotransferase in mucinous adenocarcinoma. *Glycobiology*. vol. 10, No. 9 pp. 919-929 (2000).

Streeter et al., Immunohistologic and Functional Characterization of a Vascular Addressin Involved in Lymphocyte Homing into Peripheral Lymph Nodes. *The Journal of Cell Biology*. vol. 107 pp. 1854-1862 (1988).

Supplementary European Search Report for European Patent Application No. 04747273.3-1233 PCT/JP2004009805 dated Apr. 18, 2008.

Yeh et al., Novel Sulfated Lymphocyte Homing Receptors and Their Control by a Core1 Extension B1, 3-N-Acetylglucosamineyltransferase. *Cell*. vol. 105 pp. 957-969 (2001).

Kannagi et al., "Immunological molecules recognizing carbohydrates specificity and involvement in pathology," Molecular Medicine. vol. 36, No. 8 pp. 874-886 (1999).

International Preliminary Report on Patentability (Chapter I of the Patent Cooperation Treaty) corresponding to International Patent Application No. PCT/JP2004/009805 dated May 8, 2006.

International Preliminary Report on Patentability (Chapter I of the Patent Cooperation Treaty) corresponding to International Patent Application No. PCT/JP2005/023015 dated Jul. 24, 2007.

International Search Report corresponding to International Patent Application No. PCT/JP2004/009805 dated Sep. 28, 2004.

Official Action corresponding to U.S. Appl. No. 12/567,944 dated Oct. 7, 2010.

Abstract of the 22$^{nd}$ Research Meeting of Japan Molecular Tumor Maker. pp. 42-43 (2002).

Genbank Accession No. AB011451.1. Mus musculus mRNA for N-acetylglucosamine-6-O-sulfotransferase, complete cds. Uchimura et al., "Molecular cloning and characterization of an N-acetylglucosamine-6-O-sulfotransferase," J. Biol. Chem. vol. 273, No. 35 pp. 22577-22583 (1998).

Genbank Accession No. AF131235. *Homo sapiens* N-acetylglucosamine 6-O-sulfotransferase mRNA, complete cds. Bistrup et al., "Sulfotransferases of two specificities function in the reconstitution of high endothelial cell ligands for L-selectin," J. Cell Biol. vol. 145, No. 4 pp. 899-910 (1999).

Genbank Accession No. AF176838.1. *Homo sapiens* intestine N-acetylglucosamine 6-O-sulfotransferase (I-GlcNAc-6-ST) mRNA, complete cds. Lee et al., "Cloning and characterization of a mammalian N-acetylglucosamine-6-sulfotransferase that is highly restricted to intestinal tissue," Biochem. Biophys. Res. Commun. vol. 263, No. 2 pp. 543-549 (1999).

Genbank Accession No. NM_004267. *Homo sapiens* carbohydrate (N-acetylglucosamine-6-O) sulfotransferase 2 (CHST2), mRNA. Ross et al., "Genetic variants in TPMT and COMT are associated with hearing loss in children receiving cisplatin chemotherapy," Nat. Genet. vol. 41, No. 12 pp. 1345-1349 (2009).

Genbank Accession No. NM_005769. *Homo sapiens* carbohydrate (N-acetylglucosamine 6-O) sulfotransferase 4 (CHST4), transcript variant 1, mRNA, Seko et al., "N-Acetylglucosamine 6-O-sulfotransferase-2 as a tumor marker for uterine cervical and corpus cancer," Glycoconj. J. vol. 26, No. 8 pp. 1065-1073 (2009).

Genbank Accession No. NM_012126.1. *Homo sapiens* carbohydrate (N-acetylglucosamine 6-O) sulfotransferase 5 (CHST5), transcript variant 1, mRNA. de Graffenried, C.L.,a nd Bertozzi, C.R., "Golgi localization of carbohydrate sulfotransferases is a determinant of L-selectin ligand biosynthesis," J. Biol. Chem. vol. 278, No. 41 pp. 40282-40295 (2003).

Kannagi, "Monoclonal Anti-Glycosphingolipid Antibodies," Methods in Enzymology. vol. 312 pp. 160-179 (2000).

Kannagi, "Use of Liposomes Containing Carbohydrates for Production of Monoclonal Antibodies," Methods in Molecular Biology. vol. 199 pp. 203-218. (2002).

Uchimura et al., "Human N-Acetylglucosamine-6-*O*-Sulfotransferase Involved in the Biosynthesis of 6-Sulfo Sialyl Lewis X: Molecular Cloning, Chromosomal Mapping, and Expression in Various Organs and Tumor Cells," J. Biochem. vol. 124 pp. 670-678 (1998).

* cited by examiner

Figure 4

BD PharMingen Technical Data Sheet

Page 1 of 2

PURIFIED RAT ANTI-MOUSE PNAd CARBOHYDRATE EPITOPE (CD62L Ligand) MONOCLONAL ANTIBODY

PRODUCT INFORMATION

Catalog Number: 553863 (Was: 09961D), 0.5 mg
Description: Purified anti-mouse PNAd Carbohydrate Epitope (CD62L Ligand)
Clone: MECA-79
Immunogen: Collagenase-dispersed BALB/c lymph node stroma[1]
Isotype: Rat (Wistar) IgM, κ
Contents: Purified Immunoglobulin in 10 mM phosphate buffer, pH 7.2 with 500 mM NaCl and 0.09% (w/v) sodium azide.

SPECIFICITY

The MECA-79 antibody reacts with sulfate-dependent carbohydrate epitopes of peripheral lymph node addressin (PNAd).[2] The MECA-79-reactive antigen is closely associated with the carbohydrate ligands for L-selectin (e.g., CD34, GlyCAM-1, MAdCAM-1), which are expressed on high endothelial venules (HEV) in lymphoid tissues and at sites of chronic inflammation.[1,2,3,4,5,6] Cross-reactivity with human,[3,4] ovine,[7] bovine,[7] primate,[7] and porcine[8] tissues has been observed. MECA-79 antibody inhibits L-selectin- dependent lymphocyte and platelet homing to lymph nodes in vivo[1,9] and in vitro adhesion to lymphoid tissue HEV[1,4] and immobilized PNAd.[3,9,10]

PREPARATION AND STORAGE

The antibody was purified from tissue culture supernatant by affinity chromatography. The antibody solution should be stored undiluted at 4°C.

USAGE

This antibody has been tested by immunohistochemical staining (IHC) of citrate-pretreated formalin-fixed paraffin-embedded sections (5 - 20 μg/ml) to assure specificity and reactivity. Other reported applications include IHC of acetone-fixed frozen sections,[1,4,5] immunoprecipitation[2,3] western blot analysis,[10] and in vitro and in vivo adhesion blocking.[1,3,4,9,10] Since applications vary, each investigator must determine dilutions appropriate for individual use.

Caution: Sodium azide is a reversible inhibitor of oxidative metabolism; therefore, antibody preparations containing this preservative agent must not be used in cell cultures nor injected into animals. Sodium azide may be removed by washing stained cells or plate-bound antibody or dialyzing soluble antibody in sodium azide-free buffer. Since endotoxin may also affect the results of functional studies, we recommend the NA/LE™ (No Azide/Low Endotoxin) antibody format for in vitro and in vivo use.

REFERENCES

1. Streeter, P.R., B.T.N. Rouse, and E.C. Butcher. 1988. Immunohistologic and functional characterization of a vascular addressin involved in lymphocyte homing into peripheral lymph nodes. J. Cell Biol. 107: 1853 - 1862.
2. Hemmerich, S, E.C. Butcher, and S.D. Rosen. 1994. Sulfation-dependent recognition of high endothelial venules (HEV)-ligands by L-selectin and MECA 79, an adhesion-blocking monoclonal antibody. J. Exp. Med. 180: 2219 - 2226.
3. Berg, E.L., M.K. Robinson, R.A. Warnock, and E.C. Butcher. 1991. The human peripheral lymph node vascular addressin is a ligand for LECAM-1, the peripheral lymph node homing receptor. J. Cell Biol. 114: 343 - 349.
4. Michie, S.A., P.R. Streeter, P.A. Bolt, E.C. Butcher, and L.J. Picker. 1993. The human peripheral lymph node vascular addressin. An inducible endothelial antigen involved in lymphocyte homing. Am. J. Pathol. 143: 1688 - 1698.
5. Faveeuw, C., M.-C. Cagnerault, and F. Lepault. 1994. Expression of homing and adhesion molecules in infiltrated islets of Langerhans and salivary glands of nonobese diabetic mice. J. Immunol. 152: 5969 - 5978.

Please see Page 2.

Figure 5

REFERENCES (Continued)

6. Maly, P., A.D. Thall, B. Petryniak, C.E. Rogers, P.L. Smith, R.M. Marks, R.J. Kelly, K.M. Gersten, G. Cheng, T.L. Saunders, S.A. Camper, R.T. Camphausen, F.X. Sullivan, Y. Isogai, O. Hindsgaul, U.H. von Andrian, and J.B. Lowe. 1996. The $\alpha(1,3)$fucosyltransferase Fuc-TVII controls leukocyte trafficking through an essential role in L-, E-, and P-selectin ligand biosynthesis. *Cell* 86: 643 - 653.
7. Butcher, E.C. Personal communication.
8. Binns, R.M., A. Whyte, S.T. Licence, A.A. Harrison, Y.T.M. Tsang, D.O. Haskard, and M.K. Robinson. 1996. The role of E-selectin in lymphocyte and polymorphonuclear cell recruitment into cutaneous delayed hypersensitivity reactions in sensitized pigs. *J. Immunol.* 157: 4094 - 4099.
9. Diacovo, T.G., K.D. Puri, R.A. Warnock, T.A. Springer, and U.H. von Andrian. 1996. Platelet-mediated lymphocyte delivery to high endothelial venules. *Science* 273: 252 - 255.
10. Puri, K.D., E.B. Finger, G. Gaudernack, and T.A. Springer. 1995. Sialomucin CD34 is the major L-selectin ligand in human tonsil high endothelial venules. *J. Cell Biol.* 131: 261 - 270.

For Research Use Only. Not For Diagnostic or Therapeutic Use.

Conditions: BD PharMingen will not be responsible for violations or patent infringements which may occur with the use of our products.

Hazardous Ingredient: Sodium Azide. Avoid exposure to skin and eyes, ingestion, and contact with heat, acids, and metals. Wash exposed skin with soap and water. Flush eyes with water. Dilute with running water before discharge into plumbing.

METHOD FOR EXAMINING CARCINOMA AND ADENOMA

CROSS REFERENCE TO RELATED APPLICATIONS

This application is a National Stage of International Application No. PCT/JP2005/023015, filed Dec. 15, 2005, and which claims benefit of Japanese Patent Application No. 2005-011151 filed Jan. 19, 2005, which are incorporated herein in their entirety.

REFERENCE TO A SEQUENCE LISTING

A Sequence Listing containing SEQ ID NOS.: 1-6 is incorporated herein by reference.

FIELD OF THE INVENTION

The present invention relates to examining methods of human carcinomas and adenomas except colorectal carcinomas and colorectal adenomas and to examination reagents thereof.

PRIOR ART

Since the number of carcinoma patients is increasing year by year, a method for early detection is necessary. Although, immunological fecal occult blood test and various tumor markers are used at present for the examination of carcinomas, these methods do not have satisfactory positive rates. Namely, the positive rate of immunological fecal occult blood test used for the examination of carcinomas and adenomas is 50 to 60%. As to the tumor markers of colorectal carcinomas, carcino-embryonic antigen (CEA), CA19-9, STX, which are used for examining the therapeutic effect and for monitoring recurrence, are not satisfactory as tumor markers for early detection of colorectal carcinomas.

Although sulfation of sugar residues is active in a normal large bowel, it is known that the sulfation of sugar residues is remarkably reduced in colorectal carcinomas. Namely, both 3'-sulfation of galactose and 6-sulfation of N-acetylglucosamine (hereinafter referred to as [GlcNAc]), which are abundant in colorectum, are reduced (Reference 1). A number of GlcNAc-6-sulfotransferase isozymes have been known in colorectal carcinoma tissues and in non-carcinoma colorectal tissues of patients, and I-GlcNAc6ST is significantly decreased in course of carcinogenesis, which leads to the reduced sulfation of sugar residues in colorectal carcinoma (Reference 2). While, GlcNAc6ST-1, one of the isozymes in a normal colorectum, does not show significant changes in the level in course of carcinogenesis. Furthermore, HEC-GlcNAc6ST, another isozyme, increases significantly in carcinoma (Reference 3).

HEC-GlcNAc6ST, which increases in carcinomas, synthesizes 6-sulfated GlcNAc and carries out sulfation of GlcNAc in various sugar residues. Therefore, there are a huge variety of the structures of intra-cellularly synthesized sugar residues and their antigenicity. Since GlcNAc6ST-1 and I-GlcNAc6ST also synthesize 6-sulfated GlcNAc, only the fact that 6-sulfated GlcNAc is synthesized from HEC-GlcNAc6ST cannot be used as a specific method for diagnosis of carcinomas and adenomas. However, it is known that the substrate selectivity of GlcNAc6ST-1 and I-GlcNAc6ST is more specific than that of HEC-GlcNAc6ST (References 3, 4). Therefore, certain 6-sulfated sugar residues might be produced by HEC-GlcNAc6ST, but not by GlcNAc6ST nor by I-GlcNAc6ST (Reference 5). However, an actual system for diagnosis of carcinomas and adenomas has not been established.

On the other hand, the monoclonal antibody (MECA-79 antibody, Reference 6), commercially available as an antibody against an immunological homing receptor of lymphocytes, is known to react with chemically synthesized GlcNAc6-sulfated sugar residues (Reference 7). Moreover, the antigens recognizable by the antibody (MECA-79) are reported to emerge on the cell surface, when a mouse gene encoding HEC-GlcNAc6ST enzyme is transduced into CHO cells (hamster ovary cells) (Reference 8).

The present inventors found that human colorectal carcinoma cells has the antigen recognizing the MECA-79 antibody, which could be applied for the examination of colorectal carcinomas and colorectal adenomas (Patent application 2003-296216, PCT/JP2004/009805).

Reference 1: Izawa, M. et al., Cancer Res., 60: 1410-1416, 2000.
Reference 2: Abstract of the 22nd Research Meeting of Japan Molecular Tumor Maker pp 42-43, 2002.
Reference 3: Seko, A. et al., Glycobiology, 10:919-929, 2000
Reference 4: Seko, A. et al., Glycobiology, 12:379-388, 2002
Reference 5: The Journal of Biological chemistry, vol. 277, No. 6, 3979-3984 (2002)
Reference 6: Streeter, P. R. et al., J. Cell Biol. 107: 1853-1862, 1988.
Reference 7: Bruehl, R. E. et al., J. Biol. Chem. 275: 32642-32648, 2000
Reference 8: Yeh, J. C. et al., Cell 105: 957-969, 2001.

Problems to be Solved by the Invention

The present invention provides examination methods and reagents of carcinomas and adenomas, wherein the method enables to detect efficiently carcinoma and adenoma patients and patients (except colorectal carcinomas and colorectal adenomas) at high risk of carcinomas and is useful for diagnosis of carcinomas and adenomas.

Means to Solve the Problems

The present inventors discovered that there are significant differences in the distribution of GlcNAc-6-sulfotransferase isozymes, sulfation enzymes of sugar residues, between non-carcinoma tissues and carcinoma tissues or adenoma tissues, during investigations. Then the inventors found that carcinomas and adenomas (except colorectal carcinomas and colorectal adenomas) could be detected specifically by assaying 6-sulfated sugar residues, which are synthesized only by HEC-GlcNAc6ST, but not by GlcNAc6ST-1 nor by I-GlcNAc6ST, in tissues of patients and in fecal samples.

Previously, many antibodies such as AG223 (Biochem. (Tokyo), 124:670-678, 1998), G152, G72, AG97, AG107, AG273, G2706, G27011, G27039 (the above: J. Biol. Chem., 273: 11225-11233, 1998) and the like have been known to react with GlcNAc-6-sulfated sugar residues. Meanwhile, MECA-79 antibody (Pharmingen, Catalog No. 09961D; Distributor, Becton, Dickinson and Company), which is available commercially as an antibody against lymphocyte immunological homing receptor, has been known to react with some kinds of GlcNAc-6-sulfated sugar residues (Reference 6). The present inventors screened to look for antibodies, which are weakly or little reactive to cells expressing GlcNAc-6-sulfated sugar residues found in normal cells, but are reactive with cells expressing GlcNAc-6-sulfated sugar residues increased in carcinoma cells, examined the reactivity of the antibodies to samples from patients, found that these antibodies are highly positive to various carcinoma cells and completed the present invention.

In other words, the present invention is a method for examining carcinomas and adenomas, except colorectal carcinomas and colorectal adenomas, comprising assaying presence or absence, or intensity of the reactivity of an antibody to tissues, body fluid or feces of patients, or extracts thereof, wherein said antibodies react with such antigen that is present in cells expressing HEC-GlcNAc6ST gene encoding GlcNAc-6-sulfotransferase and that is absent or almost absent in cells expressing GlcNAc6ST-1 or 1-GlcNAc6ST gene.

The antigen may be an antigen that is present in cells transduced with HEC-GlcNAc6ST gene and is absent or almost absent in cells transduced with GlcNAc6ST-1 gene or I-GlcNAc6ST gene.

The antigen comprises the sugar residues expressed by the following formula:

R1-Gal β1-3/4(SO$_3$-6)GlcNAc β1-R2 where, R1 represents sugar residues added by other enzymes and is not limited in structure, Gal β represents β galactose, GlcNAc β represents β N-acetylglucosamine, Gal β1-3/4 represents binding of 1 position of Gal β and 3 position and/or 4 position of GlcNAc β, (SO$_3$-6) represents addition of a sulfate group to 6 position of GlcNAc β, R2 represents -3GalNAc α, -3Gal β or -2Manα and binds to 1 position of GlcNAc β.

Furthermore, the present invention is a method for examining carcinomas and adenomas, except colorectal carcinomas and colorectal adenomas, comprising assaying the reactivity of MECA-79 antibody (Pharmingen, catalog No. 09961D) or its equivalent with tissues, body fluid, feces or extract thereof of test subjects.

Moreover, the present invention is any one of the above methods, further comprising reacting a labeled probe to said antibody and assaying the label qualitatively or quantitatively.

The preferable examination method comprises fixing the antigens present in tissues, body fluid or feces or extracts thereof of patients to a membrane, reacting with the antibody, reacting with a labeled probe and detecting the label. It is preferable to insert washing procedures appropriately between the above processes. The above probe includes anti-human-IgG antibody, protein G, protein A, and protein L. These probes are usually labeled. The labels include a radioactive isotope ($^{125}$I) and enzymes (peroxidase, alkaline phosphatase). An antibody with enzyme may involve observation of a change (i.e. color change) by the reaction between the enzyme and the substrate.

Still furthermore, the present invention is an examination reagent for carcinomas and adenomas, except colorectal carcinomas and adenomas, comprising, as a major component, an antibody reacting specifically with an antigen carrying sugar residues, which is present in cells expressing HEC-GlcNAc6ST gene and is absent or almost absent in cells expressing GlcNAc6ST-1 or GlcNAc6ST gene.

Still moreover, the present invention is an examination reagent for carcinomas and adenomas, except colorectal carcinomas and adenomas, comprising, as a major component, an antibody reacting specifically with an antigen carrying sugar residues, which is present in cells transduced with HEC-GlcNAc6ST gene and is absent or almost absent in cells transduced with GlcNAc6ST-1 or GlcNAc6ST gene.

Also, the present invention is an examination reagent for carcinomas and adenomas, except colorectal carcinomas and colorectal adenomas, comprising, as a major component, an antibody reacting specifically with an antigen carrying sugar residues, which are present in tissues, body fluid or feces of patients with colorectal cancer and colorectal adenoma and expressed by the following general formula:

R1-Gal β61-3/4(SO$_3$-6)GlcNAc β1-R2 where, R1 represents sugar residues added by other enzymes and is not limited in structure, Gal β represents β galactose, GlcNAc β represents β N-acetylglucosamine, Gal β1-3/4 represents binding of 1 position of Gal β and 3 position and/or 4 position of GlcNAc β, (SO$_3$-6) represents addition of a sulfate group to 6 position of GlcNAc β, R2 represents -3GalNAc α, -3Gal β or -2Manα and binds to 1 position of GlcNAc β.

BRIEF DESCRIPTION OF THE DRAWINGS

FIG. 4 shows a catalog of MECA-79 antibody (Pharmingen, catalog No. 09961D).

FIG. 5 shows a catalog of MECA-79 antibody (Pharmingen, catalog No. 09961D).

DETAILED DESCRIPTION OF THE INVENTION

Figure 1:
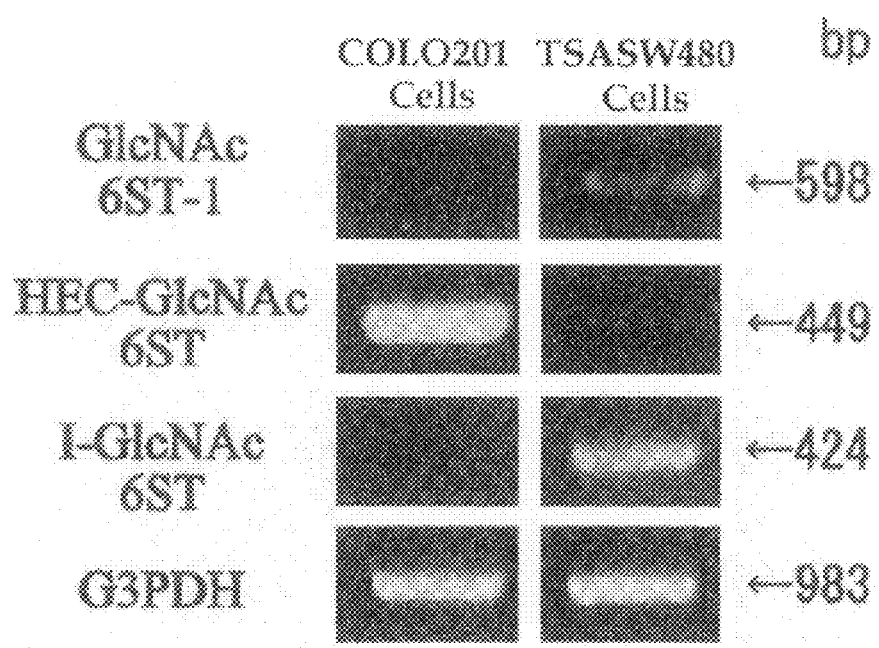
FIG. 1 shows the results of flowcytometric analysis using MECA-79 antibody on colorectal cancer cells (COLO201 cells) and on normal colorectal epithelial cells (SW480 cells treated with Tricostatine A).

The structure of 6-sulfated sugar residues, which are rarely synthesized by GlcNAc6ST-1 or by I-GlcNAc6ST, but are synthesized only by HEC-GlcNAc6ST, is represented by the following general formula:

R1-Galβ-3/4(SO$_3$-6)GlcNAcβ1-R2.

Various sugar residue carriers carry GlcNAcβ, which is the substrate of GlcNAc-6-sulfotransferase in a body. R2 is a carrier.

HEC-GlcNAc-6ST has been known to transfer sulfate residues to all kinds of GlcNAcβ1-R2 previously tested according to both our research and other peoples research (References 4 and 7). In contrast, GlcNAc6ST-1 and I-GlcNAc6ST transfer sulfate residues only to a special kind of GlcNAcβ-R2 carrying a specific form of R2.

The case, in which HEC-GlcNAc6ST but not GlcNAc6ST-1 nor I-GlcNAc6ST can transfer a sulfate residue, is known as the case that R2 is -3GalNAcα (the structure after sulfation is SO$^-_3$-6GlcNAcβ1-3GalNAcα), the case that R2 is -3Galβ(the structure after sulfation is SO$^-_3$-6GlcNAcβ1-3Galβ) and the case that R2 is -2Manα (the structure after sulfation is SO$^-_3$-6GlcNAcβ1-2Manα) (J. Biol. Chem., 277: 3979-3984, 2002 and Glycobiology, 12: 379-388, 2002). In the test method of the present invention, a specific antibody to any one of the three cases or antibodies cross reacting to all three sugar residues may be usable.

GlcNAc-6-sulfotransferase adds sulfate group to terminal GlcNAc of sugar residues and synthesizes said 6-sulfated GlcNAc (i.e. SO$^-_3$-6GlcNAc) intra-cellularly. However, after synthesis of terminal 6-sulfated GlcNAc of sugar residues, the modified sugar residues are further added with sugar residues (R1) by other enzyme groups intra-cellularly, then a large variety of the structure and antigenicity of the sugar residues are finally synthesized and are generated from cells. Generally the structure added to 6-sulfated GlcNAc is Galβ1-4 and Galβ1-3 (referred to as Galβ1-3/4). Moreover, it is known that NeuAcα2-3/6, $SO^-_3$-3/6, and Fucα1-2/3/4 are added to the 6-sulfated GlcNAc. The R1 part is added after the synthesis of 6-sulfated GlcNAc by GlcNAc-6-sulfotransferase. Therefore, R1 part is not related to the substrate specificity of such GlcNAc-6-sulfotransferases as HEC-GlcNAc6ST, GlcNAc6ST-1 and I-GlcNAc6ST.

The antigens carrying the above sugar residues are present in carcinoma tissues obtained from colorectal carcinoma patients by biopsy or by surgical operation, and in such samples as serum, ascites and feces containing the antigens derived from the above tissues. Also, the antigen may be easily extracted from these samples using phosphate buffered saline. Also, the antibody against this sugar residue antigen could be obtained by known arts producing antibodies (e.g. Methods in Enzymology, 312: 160-179, 2000; Methods in Molecular Biology, 199: 203-218, 2002 et al.). An example of these antibodies may include MECA-79 antibody (Pharmingen, Catalog No. 09961D shown in FIGS. 4 and 5).

The examination method and reagent using the antibodies of the present invention could be applied not only to colorectal carcinomas and colorectal adenomas, but also to adenomas causing universal carcinomas and precancerous states, i.e. to universal malignant tumors, i.e. to epithelial carcinomas and non-epithelial malignant tumors, preferably to epithelial carcinomas.

Malignant tumors are classified to epithelial carcinomas and non-epithelial malignant tumors. Epithelial carcinomas are classified to adenocarcinoma, squamous cell carcinoma and other epithelial carcinoma, wherein adenocarcinomas involve colorectal carcinoma, breast carcinoma, gallbladder carcinoma, gastric carcinoma, renal carcinoma, ovarian cancer, prostate carcinoma, pancreatic carcinoma, a part of pulmonary carcinoma, thyroid carcinoma, bronchial cancer, bile duct carcinoma, ovarian duct carcinoma, salivary gland cancer and testicular cancer; squamous cell carcinomas involve esophageal carcinoma, a part of pulmonary carcinoma, uterine cancer, oral carcinoma, carcinoma linguae, laryngeal cancer, pharyngeal cancer, cutaneous carcinoma, vaginal carcinoma and penile cancer; other epithelial carcinomas include hepatic carcinoma, bladder carcinoma and the like; and non-epithelial malignant tumors involve osteosarcoma, malignant melanoma, fibrosarcoma and the like as well as leukemia, malignant lymphoma and cerebral tumor.

The following Examples illustrate the present invention, but are not intended to limit the scope thereof.

Reference Example 1

Gene expression of GlcNAc-6-sulfotransferase isozymes was examined by RT-PCR on human-derived colorectal carcinoma cells (Colo201 cells) and on TSA-SW480 cells obtained by the treatment of normal colorectal epithelial cells (SW480 cells, obtained from Tohoku University, Cell Resource Center for Biomedical Research) with Tricostatin A.

In the RT-PCR analysis, PCR primers for detection of the expression of HEC-GlcNAc6ST gene (Genebank, AF131235) are synthetic oligonucleotides of SEQ ID NO. 1 for upper strand side and those of SEQ ID NO. 2 for lower strand side (Tm=59° C.), those for GlcNAc6ST-1 gene (Genebank, AB011451) are synthetic oligonucleotides of SEQ ID NO. 3 for upper strand side and those of SEQ ID NO. 4 for lower strand side (Tm=62° C.), and those for I-GlcNAc6ST gene (Genebank, AF176838) are synthetic oligonucleotides of SEQ ID NO. 5 for upper strand side and those of SEQ ID NO.6 for lower strand side (Tm=60° C.).

The results are shown in FIG. 1. It is found that the colorectal carcinoma cells (Colo 201 cells) are typical colorectal carcinoma cells, which show the pattern of strong expression of HEC-GlcNAc6ST gene and little expression of GlcNAc6ST-1 and I-GlcNAc6ST genes. Furthermore, it is found that TSA-SW480 cells are typical normal epithelial cells, which show the pattern of little expression of HEC-GlcNAc6ST gene and strong expression of GlcNAc6ST-1 and I-GlcNAc6ST genes.

Example 1 cDNA of HEC-GlcNAc6ST (Genebank, NM_005769), GlcNAc6ST-1 (Genebank, NM_004267) and I-GlcNAc6ST (Genebank, NM_012126) genes are transduced into human colorectal carcinoma cells (SW480 cells, obtained from Tohoku University, Cell Resource Center for Biomedical Research) together with drug resistant neo gene. After cloning by drug selection, said gene expression was confirmed by RT-PCR. The monitoring of gene expression was performed by regular detection of 6-sulfotransferase gene products during maintenance culturing and was used for examining stable gene expression.

A mouse was immunized by the use of said carcinoma cells by a conventional method. Then, monoclonal antibody, which reacts with those carcinoma cells transformed with GlcNAc-6-sulfotransferase gene, but does not react with those carcinoma cells transformed with other GlcNAc-6-sulfotransferase genes such as GlcNAc6ST-1 or I-GlcNAc6ST gene, was prepared. As the results, several antibodies such as KN173, KN101, KN439 and 7A4, which satisfy the above condition, were obtained.

Screening of reactivity between cells and antibodies was performed by flowcytometric analysis by the use of FACScan (Becton Dickinson) after staining cells with an indirect fluorescent antibody method (the first antibody 1.0 μg/ml, 4° C., 30 min; the second antibody: rabbit anti rat IgM antibody (Zymed Laboratories), 4° C., 30 min).

After the above-obtained monoclonal antibody was reacted at 4° C. for 30 min as the first antibody, cells were stained conventionally by the use of FITC-labeled rabbit anti mouse immunogloblin antibody (Zymed Laboratories, 4° C., 30 min) as the second antibody and were analyzed by FACScan (Becton Dickinson). The results are shown in FIG. 2.

All antibodies react only with carcinoma cells transformed with HEC-GlcNAc6ST gene and do not react with carcinoma cells transformed with GlcNAc6ST-1 or I-GlcNAc6ST gene. Furthermore, MECA-79 antibody (Pharmingen, Catalog No. 09961D) reacts slightly with GlcNAc6ST-1 gene-transformed carcinoma cells in addition to HEC-GlcNAc6ST gene-transformed carcinoma cells.

Figure 2:
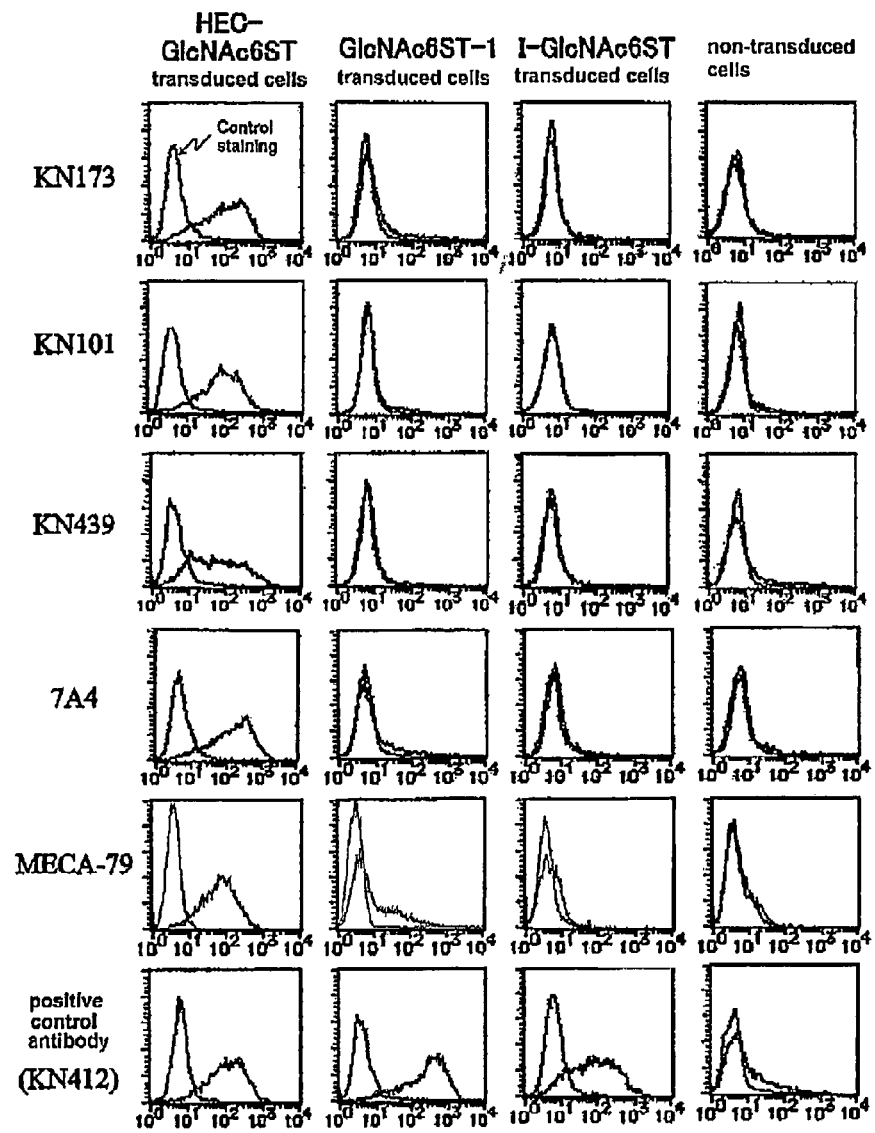
FIG. 2 shows the result of the flowcytometric analysis on the reactivity of various antibodies with cells. The ordinate shows the cell frequency (the number of cells) and the abscissa axis shows the fluorescence (Arbitrary Unit). Transfectants show transgenic cells.

Moreover, as shown in FIG. 2, positive control antibody KN412 is a general 6-sulfation antibody, which reacts with gene products of all kinds of 6-sulfotransferase genes and is a control antibody detecting gene expression of 6-sulfotransferase in gene-transformed cells.

Example 2

6-sulfated sugar residues in serum samples of various cancer patients were assayed by sandwich ELISA method by the use of antibody secreted from the clone 7A4 obtained in Example 1. First, the monoclonal antibody 7A4 secreted from the clone 7A4 is fixed in wells of a microplate. Second, serum samples of patients are reacted in the wells. Third, said biotin-labeled antibody is reacted in the wells. Forth, streptavidin-labeled Horse Radish Peroxidase is reacted in the wells. Fifth, the reactants are colored by the use of TMB substrate and finally the ratio of absorbance at 450 nm to control absorbance at 620 nm is measured to determine the amount of reactants after stopping the color development. Positive or negative is judged based on a cut-off line of average +2SD of normal people.

Figure 3:
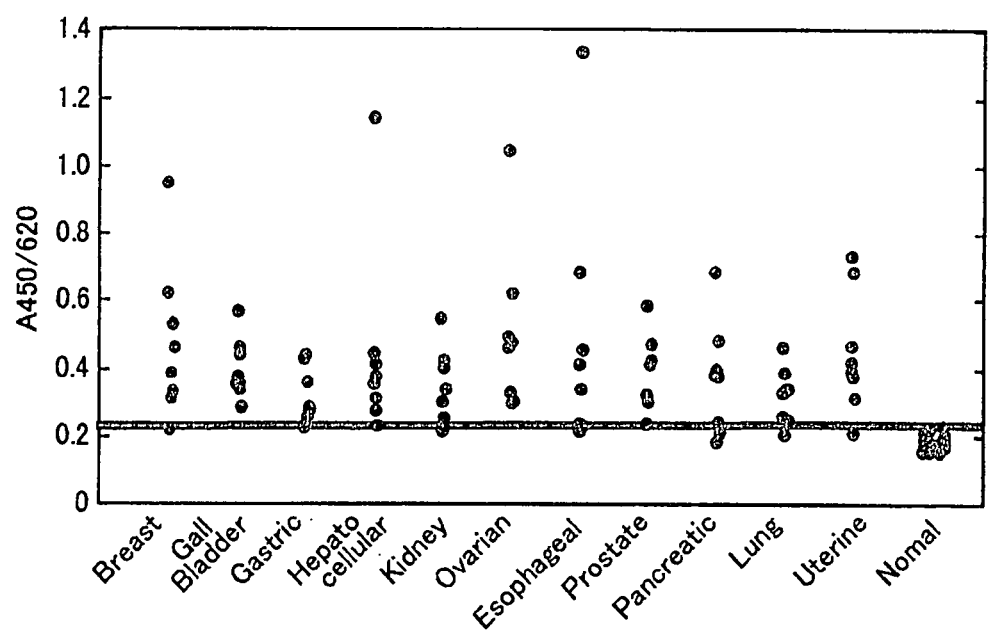
FIG. 3 shows the result of determination of the amount of sugar residues in serum samples of various carcinoma patients by sandwich ELISA method by the use of 7A4 antibody of the present invention.

The results are shown in FIG. 3. The amount of said sulfated sugar residues are increased in various carcinoma cases such as breast, pancreatic, gall bladder, esophageal, gastric, hepatocellular, kidney, prostate, lung ovarian, uterine and the like. Normal people are all negative.

What is claimed is:

1. An examination reagent for carcinomas and adenomas, except colorectal carcinomas and colorectal adenomas, comprising, as a major component, an antibody binding specifically with an antigen carrying sugar residues, which is present in cells expressing HEC-GlcNAc6ST gene and is absent or almost absent in cells expressing GlcNAc6ST-1 or I-GlcNAc6ST gene, wherein "GlcNAc6ST" refers to a family of GlcNAc-6-O-sulfotransferases, and wherein the sugar residues comprise a -Gal β1-3/4(SO$_3$-6)GlcNAc β1- region where the specific binding occurs.

2. An examination reagent for carcinomas and adenomas, except colorectal carcinomas and colorectal adenomas, comprising, as a major component, an antibody binding specifically with an antigen carrying sugar residues, which is present in cells transduced with HEC-GlcNAc6ST gene and is absent or almost absent in cells transduced with GlcNAc6ST-1 or I-GlcNAc6ST gene, wherein the sugar residues comprise a -Gal β1-3/4(SO$_3$-6)GlcNAc β1- region where the specific binding occurs.

3. An examination reagent for carcinomas and adenomas, except colorectal carcinomas and colorectal adenomas, comprising, as a major component, an antibody binding specifically with an antigen carrying sugar residues, which are present in tissues, body fluid or feces of patients with carcinomas and adenomas and expressed by the following formula:

R1-Gal β1-3/4(SO$_3$-6)GlcNAc β1-R2 where, R1 represents sugar residues added by other enzymes and is not limited in structure, Gal β represents β galactose, GlcNAc β represents β N-acetylglucosamine, Gal β1-3/4 represents binding of 1 position of Gal β and 3 position and/or 4 position of GlcNAc β, (SO$_3$-6) represents addition of a sulfate group to 6 position of GlcNAc β, R2 represents -3GalNAc α, -3Gal β or -2Manα and binds to 1 position of GlcNAc β, and wherein the specific binding occurs in the -Gal β1-3/4 (SO$_3$-6)GlcNAc β1- region of the antigen.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
gcagcatgag cagaaactca ag                                            22

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
tccaggtaga cagaagatcc ag                                            22

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgcaatgtt cctggaaggc                                               20

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ttgatgtagt tctccaggaa g                                             21

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
caagacagtg acagtgctcc                                               20

<210> SEQ ID NO 6
<211> LENGTH: 20
<212> TYPE: DNA

```
<213> ORGANISM: Artificial Sequence
<220> FEATURE:
<223> OTHER INFORMATION: primer

<400> SEQUENCE: 6
tacgtcctgc ttgctgatgg                                                   20
```